United States Patent [19]

Soloway et al.

[11] Patent Number: 5,466,679
[45] Date of Patent: Nov. 14, 1995

[54] CARBORANYL URIDINES AND THEIR USE IN BORON NEUTRON CAPTURE THERAPY

[75] Inventors: Albert H. Soloway, Worthington; Rolf F. Barth, Columbus; Abul K. Anisuzzaman, Westerville, all of Ohio; Werner Tjarks, Bremen, Germany; Feng-Guang Rong; Iwona M. Wyzlic, both of Columbus, Ohio

[73] Assignee: The Ohio State University Research Foundation, Columbus, Ohio

[21] Appl. No.: 206,750

[22] Filed: Mar. 7, 1994

Related U.S. Application Data

[63] Continuation of Ser. No. 63,913, May 17, 1993, abandoned.
[51] Int. Cl.$^6$ .......................... A61K 31/70; A61K 33/22; C07H 19/06; C07H 23/00
[52] U.S. Cl. .......................... 514/50; 514/64; 536/28.53; 424/1.11
[58] Field of Search .......................... 514/49, 50, 64, 514/4.1; 424/1.1, 1.11; 536/28.53; 530/330

[56] References Cited

U.S. PATENT DOCUMENTS

| | | | |
|---|---|---|---|
| 5,130,302 | 7/1992 | Spielvogel et al. | 514/45 |
| 5,171,849 | 12/1992 | Soloway et al. | 536/23 |
| 5,260,427 | 11/1993 | Spielvogel et al. | 536/17.1 |
| 5,362,732 | 11/1994 | Spielvogel et al. | 514/256 |
| 5,399,732 | 3/1995 | Spielvogel et al. | 558/72 |

OTHER PUBLICATIONS

Mishima et al., The J. of Investigative Dermatology, vol. 92, No. 5, Supplement, pp. 321S–325S, (1989).
Barth et al., Cancer, vol. 70, No. 12, "Boron Neutron Capture Therapy for Cancer," pp. 2995–3008 (1992).
Barth et al., Cancer Research, vol. 50, "Boron Neutron Capture Therapy of Cancer," pp. 1061–1070, (1990).
Barth et al., Scientific American, vol. 262, No. 10, "Boron Neutron Capture Therapy for Cancer," pp. 100–105, (1990).
Schinazi et al., "Boron Compound Suitable for Neutron Capture Therapy for . . . Cancer", National Cancer Institute Workshop, May 3–4, 1988.
Kabalka et al., "Boron–11 MRI and MRS of Intact Animals Infused with a Boron Neutron Capture Agent," Magnetic Resonance in Medicine V. 8, p. 231, (1988).
Schinazi et al., "Rational Design of Pyrimidines and Nucleosides for Neutron Capture Therapy," National Cancer Institute Workshop, pp. 1–11, (1988).
Yamamoto et al., J. Chem. Soc, Chem, Commun., pp. 157–158 (1992).
Wyzlic et al., Tetrahedron Letters, vol. 33, No. 49, pp. 7489–7490 (1992).
Tjarks et al., 5th Intl. Symposium on NCT for Cancer, Sep. 1992.

Primary Examiner—Douglas W. Robinson
Assistant Examiner—James O. Wilson
Attorney, Agent, or Firm—Frank H. Foster

[57] ABSTRACT

The invention relates to novel boron-containing nucleosides and amino acids which can utilize the enzymatic systems in tumor cells for incorporating such boron-containing structures into nucleic acids and proteins. Subsequent use of boron neutron capture therapy provides a method for treating tumor cells.

10 Claims, No Drawings

CARBORANYL URIDINES AND THEIR USE IN BORON NEUTRON CAPTURE THERAPY

This application is a continuation of application Ser. No. 08/063,913, filed May 17, 1993, now abandoned.

The invention herein was made with government support under Grant RO1 CA 53896 awarded by the National Cancer Institute and Grants DE-FG02-90ER60972 and ACO2-76CH00016 awarded by the Department of Energy. The government has certain rights in this invention.

TECHNICAL FIELD

This invention relates to certain 5'-carboranyl uridines, 3-carboranyl glucoses, 5-carboranyl substituted-2'-deoxyuridines, carboranyl amino acids, and 5-S-alkyl carboranyl uridines and their usage in boron neutron capture therapy (BNCT).

BACKGROUND ART

Boron neutron capture therapy (BNCT) for the treatment of mammalian tumors (e.g. cancerous tumor cells) is based on the nuclear reaction between thermal neutrons and boron-10 to yield alpha particles and lithium-7 nuclei:

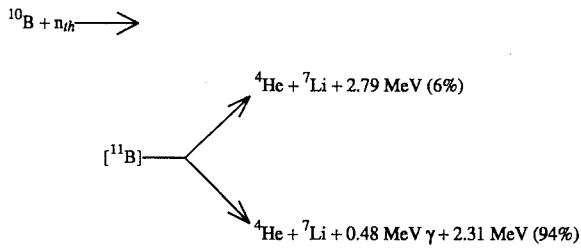

The high linear energy transfer (LET) alpha particles released in this nuclear reaction have a range in tissue of about 10 μm, approximately equal to the diameter of a single cell. Their destructive effect is, therefore, highly localized to boron-loaded tissue. A key requirement of BNCT is the selective delivery of an adequate concentration of boron-10 to tumors (15–30 μg $^{10}$B/g tumor). The lack of boron compounds with the requisite biological properties has been a major limitation for the clinical use of BNCT. Boronated analogues of compounds that are known to localize in various tumors (amino acids, thiouracils, chlorpromazine, nucleosides, antibodies, etc.) have been the focus of compound development in this area. The rationale for the synthesis of boron-containing nucleosides is that such structures would be conserved by rapidly proliferating tumor cells and phosphorylated by cellular kinases to mononucleotides. These may persist "locked-in" within the tumor cell or possibly be converted to the active precursors of nucleic acids, the di- and triphosphate forms.

A recent review article on BNCT can be found in Barth et al., "Boron Neutron Capture Therapy for Cancer—Realities and Prospects", Cancer, Vol. 70, No. 12, Dec. 15, 1992, pp. 2995–3007. Other reviews are Rolf F. Barth, Albert H. Soloway and Ralph G. Fairchild, "Boron Neutron Capture Therapy of Cancer", Cancer Research, Vol. 50, Feb. 15, 1990, pp. 1061–1070, and Rolf F. Barth et al., "Boron Neutron Capture Therapy for Cancer", Scientific American, Vol. 262, No. 10, October 1990, pp. 100–107. In the latest review on pages 3001–3003 the use of BNCT clinically in the treatment of malignant brain tumors and melanoma is described by Yutaka Mishima and his associates, including working with Duroc pigs and injecting a boron compound around a skin-level melanoma, following with exposure to thermal neutrons, and after several months noting that the melanomas began to shrink and eventually disappeared, reported in The Journal of Investigative Dermatology, Vol. 92, No. 5, Supplement, May 1989, 321S–325S. The "Scientific American" review in the paragraph bridging pages 106–107 also reports achieving through BNCT of a cure of primary melanomas on two patients.

The first mentioned review (i.e. Cancer, supra) on pages 2997–2998 lists some current boron compounds either being used or potentially useful as capture agents for BNCT therapy. Included in that listing is a 5-borono-2'-deoxy uridine, which compound contains a single B atom linked to its nucleic acid moiety of the nucleoside.

OBJECTS OF THE INVENTION

Since prior BNCT-used nucleosides generally contained a single boron atom or a carborane attached directly to the pyrimidine base moiety at the 5 position and such a bulky group may interfere with the enzymatic incorporation of this boronated nucleoside in tumor DNA, one objective of this invention was to develop boron-containing nucleosides and amino acids which could utilize the enzymatic systems in tumor cells for incorporating such structures into nucleic acids and proteins. Thus the objective of this invention was to incorporate or link a carboranyl moiety to the sugar moiety of the nucleoside, or to the 5 position on the uridine base, or to an amino acid, and to thereby provide not only a significant increase in boron content so as to enhance subsequent reaction between neutrons and boron-10, but to covalently incorporate such compounds into tumor biomolecules. Another objective was to synthesize novel, non-toxic, lipophilic, boron-containing compounds such as, carboranyl and dihydroxyboryl compounds which can traverse cell walls to deliver high levels of boron into tumors.

Still another object of the present invention was to provide an improved method of treating tumor cells using the boron neutron capture therapy.

Other objects and advantages will be apparent to one of skill in the art from the disclosure and claims which follow.

BRIEF DISCLOSURE OF INVENTION

The invention includes BNCT capture compounds which incorporate a boron-containing compound with a carboranyl or dihydroxyboryl moiety into or on a portion of a nucleoside or an amino acid. The invention also provides a method for treating tumor cells by exposing the tumor cells to increased levels of boron by means of administering various novel boron-containing compounds, followed by exposure to irradiation, such as thermal or epithermal neutrons. These boron-containing nucleosides and amino acids are believed to be novel and also to possess: (1) a tenfold increase in boron content compared to prior art single boron atom nucleosides; (2) enhanced lipophilicity for cellular penetration due to the boron-containing moiety; (3) cellular entrapment and retention properties of nucleosides in proliferating tumor cells due to the action of kinases; and (4) a retained capacity when incorporated into an oligonucleotide to hybridize strongly with RNA and DNA sequences since the base component would be naturally-occurring.

In one embodiment, the invention includes a novel carboranyl uridine of the structure

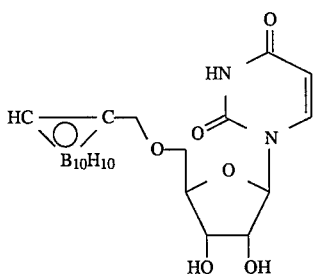

FIG. 1 and diethyl ether adducts of the carboranyl uridine. This novel boronated uridine is 5'-O-(o-Carboran-1-ylmethyl)uridine.

The invention also includes a novel boronated glucose of the structure

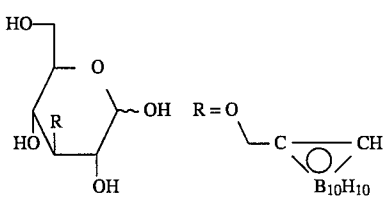

FIG. 2

This novel boronated compound is 3-O-(o-Carborany-1-ylmethyl)-D-glucose.

The invention further relates to two 5-substituted-2'-deoxyuridines of the structures

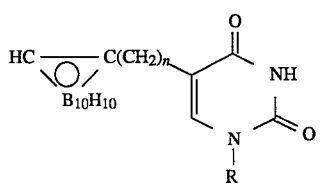

FIG. 3

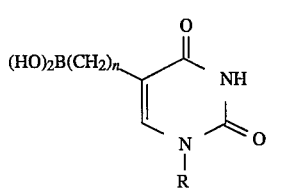

FIG. 4 wherein R=is selected from 2-deoxyribose and 2-deoxy-D-ribofuranose, and n=4 to 10. FIG. 3 represents the compound 5-[6-(1,2-dicarba-closo-dodecaboran(12)-1-yl)hexyl]-2'-deoxyuridine, but the alkyl tether can also be butyl, pentyl, heptyl, octyl, nonyl, or decyl. FIG. 4 represents the compound 5-[6-dihydroxyborylhexyl]-2'deoxyuridine, but the alkyl tether can also be butyl, pentyl, heptyl, octyl, nonyl, or decyl. In FIGS. 3 and 4, n is an integer preferably selected from 5, 6, 7, and 8, however shorter and longer spacers or tethers, whether hydrocarbon or other, are useful herein if the spacers facilitate subsequent incorporation of the boron into tumor cell DNA or RNA.

The present invention further relates to novel boronated amino acids shown in FIGS. 5, 6, and 7.

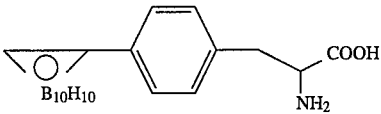

FIG. 5

CBPA

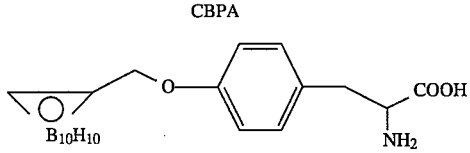

FIG. 6

CBT

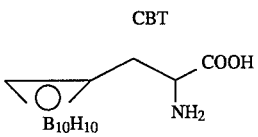

FIG. 7

CBA

FIG. 5 represents p-(o-carboran-1-yl)-phenylalanine, also called CBPA. FIG. 6 represents O-(o-Carboran-1-ylmethylmethyl)-tyrosine, also called CBT. FIG. 7 represents o-carboranylalanine, also called CBA. Related synthesis has been previously reported (Leukart et al., *Helv. Chim. Acta.*, Vol. 59, 1976, p. 2184) but the method of synthesis was not suitable for preparing large amounts of this compound. The present invention presents improved methods of synthesis.

The invention also includes 5-S-alkyl carboranyl uridines with tether groups of varying alkyl chain lengths between the sulfide bond in the 5-position of the pyrimidine base and a dihydroxyboryl moiety or carborane cage. FIGS. 8, 9 and 10 represent examples of such compounds with 5, 7, and 8, respectively, methylene units in the alkyl chain.

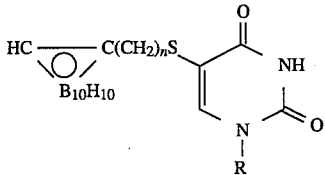

FIG. 8 represents 5-[6-(1,2-dicarba-closo-dodecaboran(12)-1-ylpentylthio]-2'-deoxyuridine, FIG. 9 represents 5-[6-(1,2-dicarba-closo-dodecaboran(12)-1-ylheptylthio]-2'-deoxyuridine, and FIG. 10 represents 5-[6-(1,2-dicarba-closo-dodecaboran(12)-1-yloctylthio]-2'-deoxyuridine.

Other thio derivatives useful in this invention can include, for example, the following tether group homologues: butyl, hexyl, nonyl, and decyl. The tether group between the boron moiety and the nucleoside can include not only an alkyl chain of varying length from four carbons up to about ten carbons, but may according to the present invention, contain an amide, ester or ether linkage, or combinations thereof. The purpose of this tethering chain is to project the boron moiety sufficiently far from the nucleoside so that enzymatic conversions to the nucleotide, di- and triphosphates and action by DNA polymerase for incorporating into tumor DNA is not inhibited. This distance is thought to be a length of from about 5 to 20 Ångstroms, preferably 8 to 12

Ångstroms. In this manner, the present invention provides boron-containing nucleosides which do not interfere with the normal enzymatic reactions and can be utilized in pyrimidine salvage pathways, by kinases and polymerases for incorporating such structures into nucleic acids. Examples of additional structures also included in the present invention are shown in FIG. 11, including examples of an amide tether, a dihydroxyboryl amino acid, and a dihydroxyboryl derivative of a thio-tethered uridine. In FIG. 11, n=4 to 10 and R=is selected from 2-deoxyribose and 2-deoxy-D-ribofuranose.

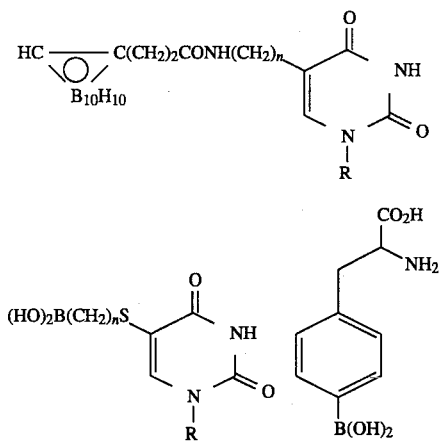

The invention also includes a method of boron neutron capture therapy of mammalian tumor cells comprising:

a) introducing to tumor cells a boron-containing compound, such as a dihydroxyboryl or carboranyl nucleoside compound in which the boron moiety is tethered to the nucleoside through a flexible linear organic chain selected from the group consisting of methylene groups, an ether linkage, an ester linkage, an amide linkage, and an alkyl sulfide group, or a combination thereof, wherein the tether is from about 5 to about 20 Ångstroms, and preferably 8 to 12 Ångstroms in length, in a manner and for a time effective to be retained by the tumor cells; and b) irradiating with neutrons said carboranyl or dihydroxyboryl nucleoside compound retained in said tumor cells. In this manner, the BNCT yields significantly increased amounts of alpha particles and lithium-7 nuclei into the tumor cells, relative to the yield from conventional boron compounds used in BNCT. Thus, increased uptake and retention of the boron in cells can be achieved by the compounds and method of the present invention. In this manner, the present invention provides an improved method for treating tumor cells sensitive to boron neutron capture therapy.

In describing the preferred invention, specific terminology will be resorted to for the sake of clarity. However, it is not intended that the invention be limited to the specific terms so selected and it is to be understood that each specific term includes all technical equivalents which operate in a similar manner to accomplish a similar purpose. The terms are not limited but include other embodiments recognized as being equivalent by those skilled in the art.

DETAILED DESCRIPTION

The invention's carboranyl and dihydroxyboryl compounds are defined and illustrated earlier herein. The preferred compound for BNCT employment according to the present invention is a carboranyl glucose, carboranyl amino acids, or boron-containing derivatized uridines, which advantageously possess adequate hydrophilic/lipophilic properties to enable solvation in aqueous media for subsequent incorporation within the mammalian tumor cell. In particular, the compounds of the present invention have a boron moiety spaced approximately 5 to 20 Ångstroms and more preferably about 8 to 12 Ångstroms from the pyrimidine base. If the boron group is bonded directly at, for example, the 5' position on the sugar, or directly on the 5 position of the pyrimidine base, it inhibits enzyme activity and/or prevents incorporation of the boron into the desired tumor cell DNA.

Therefore, it is one object of the present invention to produce boron-containing compounds which simulate, for example, thymidine, which can cross the cell barrier and become incorporated into the tumor cell DNA. The compounds of the present invention are designed to enhance kinase binding to nucleotides by the use of spacers or tethers, such as polymethylene, between the boron moiety and the nucleic acid precursor. The binding is weak when the spacer contains less than four methylene groups. When the tether is increased to 10 Ångstroms by interposing up to 6 or 8 additional methylene or other units, there will be a substantial increase in the strength of enzyme binding.

Similarly, another object of the present invention is the production of boronated nucleosides in which the 5 position has a sulfide linkage to a series of methylene groups or their equivalent between the carborane cage and the nucleoside. Substitution at the 5 position with an alkyl chain, ether linkage, ester linkage, alkyl sulfide, amide linkage and the like, allows the nucleoside to retain its substrate characteristics for corresponding kinases and can be incorporated into DNA where the RBE of the neutron capture reaction is at least double that of the reaction occurring in the cytoplasm.

In general, the invention's carboranyl uridine compounds are prepared by a synthetic method which proceeds through the reaction of uridine derivatives containing a propynyl group attached to the oxygen of the 5'-position with a bis(acetonitrile) decaborane complex which results in the desired o-carborane-substituted uridines. The compound of FIG. 1 was obtained in high yield by acidic hydrolysis of the isopropylidene protective groups of the corresponding precursors using strongly acidic ion exchange resin ($H^+$ form). (See Scheme I)

More specifically, and as an example of the present invention, the compound of FIG. 1 was prepared as follows: A solution of 2.51 g (5.67 mmol) 6-O-benzoyl-3-O-(o-carboran-1-ylmethyl)-D-allopyranose and 1.34 g (6.25 mmol) of $NaIO_4$ was stirred for 1 hour at room temperature in 75 mL of water/ethanol (1:1, v/v), when TLC indicated the conversion of the starting material to 5-O-benzoyl-2-O-(o-carboran-1-ylmethyl)-3-O-formyl-D-ribofuranose. Subsequently, most of the ethanol was evaporated at room temperature and the remaining aqueous phase was extracted 3 × with 25 mL of diethyl ether. The combined organic layers were dried over magnesium sulfate, filtered, and evaporated to dryness. The residue was redissolved in 50 mL of acetone/7.5% HCl (1:1, v/v) and the solution was stirred at room temperature for 72 hours. TLC indicated complete conversion of 5-O-benzoyl-2-O-(o-carboran-1-ylmethyl)-3-O-formyl-D-ribofuranose to 5-O-benzoyl-2-O-(o-carboran-1-ylmethyl)-D-ribofuranose. This was dissolved in 50 mL of pyridine/$Ac_2O$ (9:1, v/v) and stirred under anhydrous conditions for 12 hours at room temperature. Removal of the solvent by distillation and purification by column chromatography yielded 2.3 (82%) of the compound of FIG. 1.

The compound of FIG. 2 was prepared from 1,2:5,6-di-O-isopropylidene-D-glucose using propargyl bromide in DMF at about 100° C. The reaction product was mixed with bis(acetonitrile) decaborane complex in toluene and the removal of the O-iso-propylidene protecting groups resulted in the formation of the compound of FIG. 2 as an anomeric mixture. (See Scheme II)

Compounds 3 and 4 are prepared by reacting 5-bromo-2'-deoxyuridine via palladium-catalyzed cross-coupling reactions with various organoboron substituted compounds. This method of cross-coupling reaction between 5-bromo-2'-deoxyuridine protected by silylation, utilizing TBDMS-Cl, and the organoboron substrates as B-alkyl-9-borabicyclo [3.3.1]nonanes (B-R-9-BBN), gave the corresponding 5-polymethylene substituted-2'-deoxyuridine boron compounds in good yield. Cleaving the protected tert-butyldimethylsilyl groups gave the desired compounds containing the carborane or dihydroxyboryl moiety.

Another object of the present invention is to produce boronated derivatives of amino acids by replacing aromatic amino acids with highly lipophilic, carborane-containing amino acids for use in crossing the blood brain barrier.

The synthesis of CBPA, CBT, and CBA, for example, (FIGS. 5, 6, and 7) involves a phase transfer alkylation of N-(diphenylmethylene) aminoacetonitrile with appropriate carborane-containing bromide or propargyl bromide. In the latter case, it is followed by boronation with a decaborane-acetonitrile complex. The carborane-containing alkylation products are hydrolyzed with 6N HCl (Schiff's base) and 70% $H_2SO_4$ (cyano function). This procedure yields a racemic mixture of the carborane-containing amino acids. (See Scheme III)

The synthesis of the sulfide alkyl derivatives of FIGS. 8, 9, and 10 were synthesized from long chain terminal acetylenic alcohols which were tosylated and then boronated by standard methods. 5-Mercaptouracil was readily S-alkylated by alkyl halides using sodium methoxide. Displacement of the tosyl group on the spacer to give the S-alkyl carboranyl uracil followed. The 2,4-TMS protected boronated base was condensed with 2-deoxy-3,5-di-O-(p-toluoyl)-alpha-D-ribofuranosyl chloride in carbon tetrachloride with zinc chloride catalyst to give 90:10 beta:alpha ratio of the 3',5'-toluoyl protected nucleosides. Deprotection of the 3' and 5' hydroxyls was accomplished with sodium methoxide at 0° C. for 3 days. (See Scheme IV)

It is contemplated that the invention's herein carboranyl uridines, glucoses, and amino acids and their diethyl ether adducts will be useful for boron neutron capture therapy (BNCT) of mammalian tumors. The tumors contemplated as subjectable to this BNCT may be malignant or benign. The contemplated mammals having such mammalian malignant and benign tumors include: horses, cows, pigs, dogs, cats, guinea pigs, hamsters, rats, mice, humans, etc. From the BNCT reviews cited supra, it will be apparent, or at least determinable without undue experimentation, from the techniques for administration of other capture compounds, various suitable dosages, administration techniques, neutron radiation levels and times and techniques, which also will be useful for the herein taught carboranyl or dihydroxyboryl uridines, glucoses, and amino acids contemplated employed as capture compounds for BNCT. For example, and contemplated as preferred embodiments, are the complexes which would render such compounds soluble in aqueous media, especially the compounds of FIGS. 1 through 10 in water or in slightly saline water and administered preferably by injection, preferably intravenously, or into the tumor mass per se or through intraarterial infusion as well as other known administrative techniques and methods. If eradication of the tumor mass is sought and contemplated, there are administered those dosage amounts of the carboranyl uridines, glucoses and amino acids effective to provide tumor cell uptake and retention of a B-10 content in the equivalent amount as taught in the art for B-10 in art-used capture compounds for providing eradication of cells. It is contemplated that lesser dosage amounts than those requisite for eradication also will be of some utility in alleviation of tumor effects, if only in aesthetic appearance as of a diminished tumor size, or even of a hindering of the growth of the tumor, following the neutron radiation in BNCT, and thus in the case of BNCT of a mammalian malignant tumor of possible prolonged life duration.

Additional details and elements of the invention will be apparent from the illustration of specific examples which follow.

To illustrate the uptake and retention of the various boron-containing compounds as taught hereinabove, there were evaluated 5'-O-(o-carboran-1-ylmethyl)uridine of FIG. 1, and 3-O-(o-carboran-1-ylmethyl)-D-glucose of FIG. 2 in F98 glioma cells. The cellular uptake of boron at 16 hours for the compound of FIG. 1 was 83.8 micrograms of boron per gram of cells. The cellular uptake of boron at 16 hours for the compound of FIG. 2 was 65.2 micrograms of boron per gram of cells. These values exhibit significant enhancement of boron uptake relative to the uptake of boron from sodium mercaptoundecahydro-closo-dodecaborane ($Na_2B_{12}H_{11}SH$) administered to the F98 glioma cells, which uptake was only about 2.0 micrograms of boron per grams of cells. This is an unexpected improvement in boron uptake and retention achieved by the present invention, relative to conventional $Na_2B_{12}H_{11}SH$.

To demonstrate whether there was cellular uptake and retention, the following procedure was used. Semiconfluent F98 glioma cells were incubated with the compound for 16 hours and after two washings with serum-free media, the cells were trypsinized, washed twice again and aliquots were analyzed for boron by Direct Current Plasma (DCP) Atomic Emission Spectroscopy. For the boron analyses there was used the following instrumentation and sample preparation for analysis:

Instrumentation

A Spectraspan VB Direct Current Plasma-Atomic Emission Spectrometer, (Model #DCP-AES, Applied Research Laboratories, Brea, Calif.) was used for the boron determinations. This instrument combines a high resolution spectrometer with a high resolution Echelle grating and prism. The plasma source is argon gas heated to a temperature of 6000°–7000° K. The instrument settings used for analysis were: wave length 249.773 nm, argon flow 7L/min sleeve 50 psi, ceramic nebulizer 20 psi, entrance slits 50–300 m, as predetermined by the manufacturer. The viewing height was 1 nm between the arms of the "V" of the inverted "Y" configuration created by the three electrodes. The liquid uptake rate was approximately 2 mL/min. The operating power, once the plasma was established, was ¯40 V in the jet power supply with a 7 amp constant current output. With the operating parameters used no background correction was needed. Integration times and gain had been optimized by the manufacturer and were preset in the computer software. These particular parameters are not user alterable.

Sample Preparation for Analysis

One to 2 mL of concentrated sulfuric acid, which was adequate for up to 1 g of tissue or cells, were added to 150×16 mm Pyrex culture tubes, and these were placed in a mineral oil bath, heated to 100° C. in an exhaust hood and stirred intermittently for one hour. Since no interference with the boron signal was found with the sulfuric acid-hydrogen peroxide cocktail, the amount of sulfuric acid used in digestion was determined by the ease of digestion for a particular sample, rather than by any specific ratio of sample weight to acid volume. The amount and type of tissue were critical factors for successful digestion. If the amount of tissue or cells approached 1 gram or more, there was more chance for overheating and loss of sample by bubbling. If sample size was small (<200 mg) there was more flexibility in terms of acid volume and digestion time.

The results for cellular uptake and retention (i.e. persistence studies) for certain compounds of this invention compared to the clinically-used $Na_2B_{12}H_{11}SH$ compound are shown in the following TABLE 1.

compound. While it is not fully known yet, and the invention is not to be so limited as to the specific basis for the superior incorporation, the greater lipophilicity of the carboranyl derivatives and the various tethers thereof in comparison to the mercaptopolyhedral borane anion may account, at least in part, for the greater incorporation.

Of importance, once a boron-containing compound has been taken up by a cell, regardless of the biochemical mechanism involved in the take-up or capture, is whether or not it is retained or is washed out into its environmental surroundings (e.g. growth or incubating media). It is apparent from these preliminary results that the invention's carboranyl compounds persist for appreciable times once incorporated into F98 glioma cells and this is in marked contrast with $Na_2B_{12}H_{11}SH$, which is rapidly removed, attaining background levels within 6–12 hours.

The preceding disclosure is intended to be illustrative and descriptive of the invention made, but the true scope and full extent of the scope of the invention is believed to be only apparent from the claims, which follow, when read in light of the preceding disclosure.

TABLE 1

| Studies | Boron Conc. in | F98 Glioma Cells | Persistence Studies | | |
|---|---|---|---|---|---|
| 48 hr. Compound | Incubating Media g/ml | Boron Conc. /g 16 hrs incubation | 12 hrs | 24 hrs B/g | 48 hrs |
| $Na_2B_{12}H_{11}SH$ | 14.6 | 4.3 | 3.1+ | .4+ | * |
| " | 58.0 | 7.2 | 2.8+ | .8+ | * |
| " | 116.0 | 26.7 | 3.4+ | 1.8+ | * |
| FIG. 1 | 13.5 | 88.9 | 23.9 | 19.3 | 10.5 |

*Not measured
+These approximate the blank value for cells-the average DCP reading being 1.3 (range .4–3.0)

The results, as shown in TABLE 1, demonstrate significantly greater incorporation of the invention's carboranyl derivative compound compared with the clinically-used Scheme I

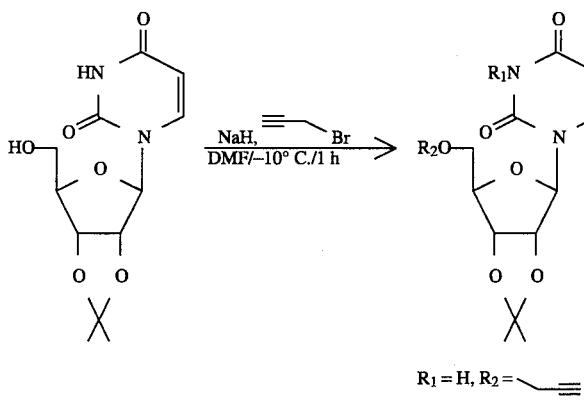

$R_1 = H, R_2 = $ ⟋≡

$CH_3CN/B_{10}H_{14}$ / toluene/90° C./5 h

Scheme I
-continued
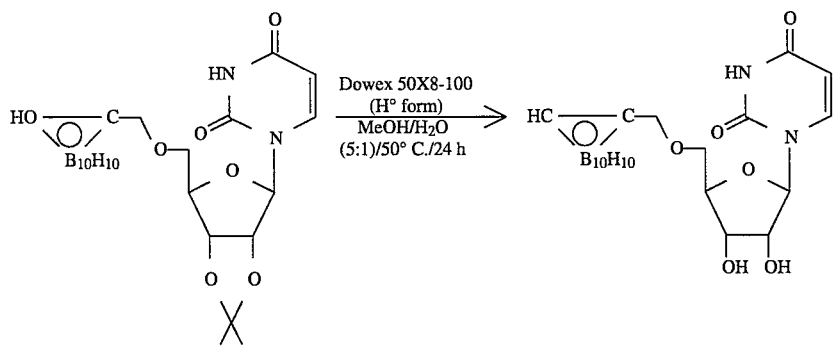
Scheme II
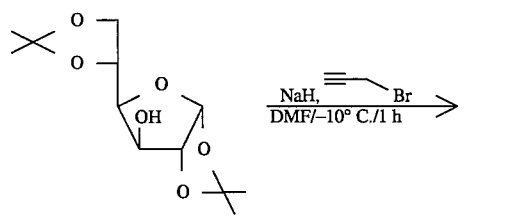
$R_1 = O-$≡  $R_2 = O-CH_2-\underset{B_{10}H_{10}}{C}=CH$
Scheme III
H—≡—CH$_2$Br  +
-continued
Scheme III
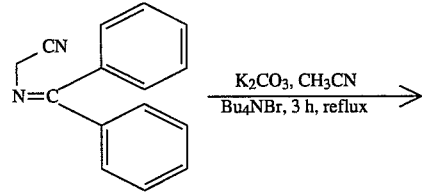
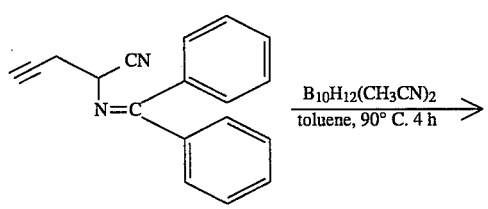
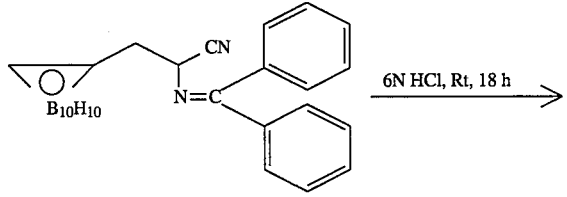
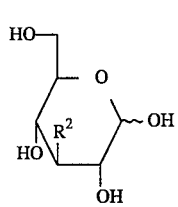
Scheme IV
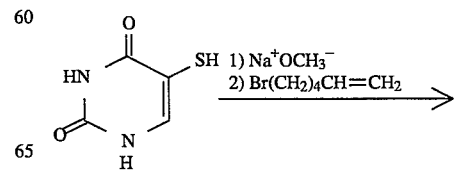

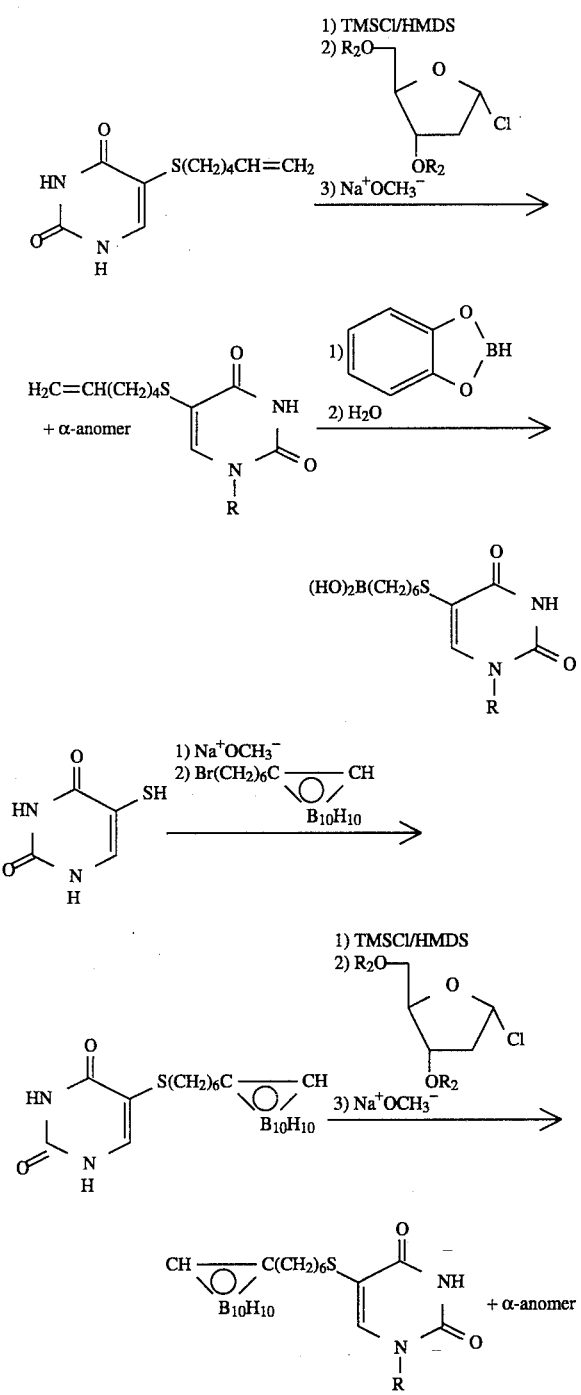

We claim:

1. A carboranyl uridine of the structure

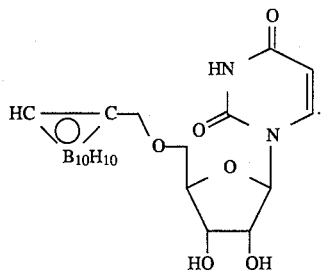

2. A 5-carboranyl substituted-2'-deoxyuridine with the structure

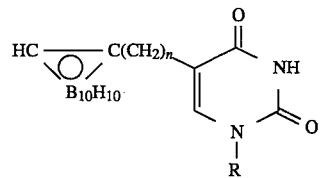

wherein R= is selected from 2-deoxyribose and 2-deoxy-D-ribofuranose, and n=4 to 10.

3. A 5-carboranyl substituted-2'-deoxyuridine with the structure

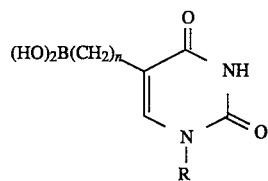

wherein R= is selected from 2-deoxyribose and 2-deoxy-D-ribofuranose, and n=4 to 10.

4. A method of boron neutron capture therapy of mammalian tumor cells comprising:

a) introducing to mammalian tumor cells by injection or intraarterial infusion a boron-containing nucleoside compound selected from the group consisting of 5'-carboranyl uridine, 5-carboranyl substituted-2'-deoxyuridine, and 5-S-alkyl carboranyl uridine, in which the boron moiety is tethered to the nucleoside through a flexible linear organic chain selected from the group consisting of methylene groups, an ether linkage, an ester linkage, an amide linkage, and an alkyl sulfide group, wherein the tether is from about 5 to about 20 Ångstroms in length, in a manner and for a time effective to be retained by the tumor cells; and b) exposing to neutron radiation said boron-containing nucleoside compound retained in said tumor cells.

5. The method of claim 4 wherein the boron-containing nucleoside compound is retained by the tumor cells in a substantially greater amount than that amount which is retained by mammalian normal, non-tumor cells.

6. A 5-S-alkyl carboranyl uridine with the structure

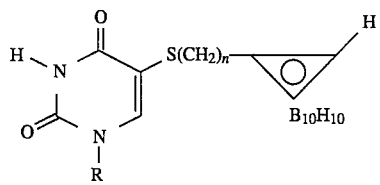

wherein R is selected from 2'-deoxyribose and 2'-deoxy-D-ribofuranose, and wherein n=4 to 10.

7. A 5-carboranyl substituted-2'-deoxyuridine with the structure

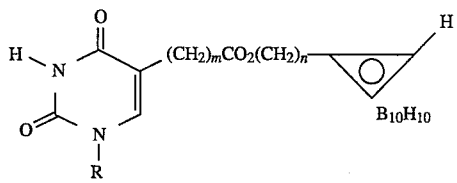

wherein R is selected from 2'-deoxyribose and 2'-deoxy-D-ribofuranose, m=2 to 4 and n=4 to 6.

8. A 5-carboranyl substituted-2'-deoxyuridine with the structure

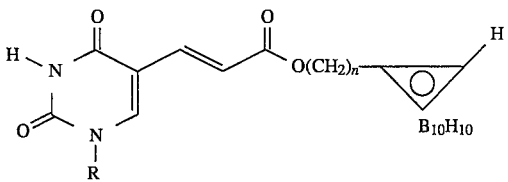

wherein R is selected from 2'-deoxyribose and 2'-deoxy-D-ribofuranose, and n=4 to 10.

9. A 5-carboranyl substituted-2'-deoxyuridine with the structure

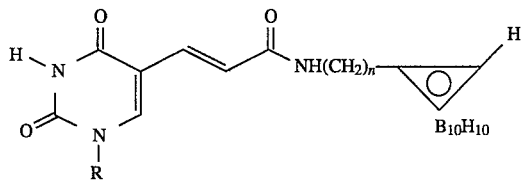

wherein R is selected from 2'-deoxyribose and 2'-deoxy-D-ribofuranose, and n=4 to 10.

10. A 5-carboranyl substituted-2'-deoxyuridine with the structure

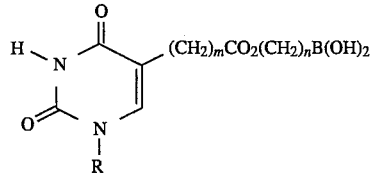

wherein R is selected from 2'-deoxyribose and 2'-deoxy-D-ribofuranose, m=2 to 4 and n=4 to 6.

* * * * *